United States Patent [19]
Pereira-Smith et al.

[11] Patent Number: 5,627,039
[45] Date of Patent: May 6, 1997

[54] MORTALIN AND METHODS FOR DETERMINING COMPLEMENTATION GROUP ASSIGNMENT OF CANCER CELLS

[75] Inventors: Olivia M. Pereira-Smith, Houston, Tex.; Renu Wadhwa, Tsukuba, Japan

[73] Assignee: Baylor College of Medicine, Houston, Tex.

[21] Appl. No.: 214,583

[22] Filed: Mar. 18, 1994

[51] Int. Cl.$^6$ .................................................. G01N 33/574
[52] U.S. Cl. ........................... 435/7.23; 435/7.21; 436/63; 436/64; 436/813
[58] Field of Search ........................ 435/7.23, 7.21; 436/63, 64, 813

[56] References Cited

PUBLICATIONS

Wadhwa, et al., *Experimental Cell Research*, vol. 216, No. 1, pp. 101–106, 1995.
Pereira-Smith, O.M. et al., " Genetic Analysis of Indefinite Division in Human cells: Identification of Four Complementation Groups," *Proc. Natl. Acad. Sci. (U.S.A.)* 85:6042–6046 (1988).
Ning, Y. et al., "Tumor Suppression by Chromosome 11 Is Not Due to Cellular Senescence," *Exper. Cell Res.* 192:220–226 (1991).
Ning, Y. et al., "Molecular Genetic Approaches to the Study of Cellular Senescence," *Mutat. Res.* 256:303–310 (1991).
Spiering, A.L. et al., "Correlation Between Complementation Groups for Immortality and DNA Synthesis Inhibitors," *Exper. Cell Res.* 195:541–545 (1991).
Ning, Y. et al., "Genetic Analysis of Indefinite Division in Human Cells: Evidence for a Cell Senescence–Related Gene(s) on Human Chromosome 4," *Proc. Natl. Acad. Sci. (U.S.A.)* 88:5635–5639 (1991).
Kwok, P.Y. et al., "Automatable Screening of Yeast Artificial–Chromosome Libraries Based on The Oligonucleotide–Ligation assay," *Genomics* 13:935–941 (1992).
Drebin, J.A. et al., "Tumor Markers In Cancer Diagnosis and Therapy," In: *Current Therapy in Oncology*, (Niederhuber, J.E., Ed.) B.C. Decker, pp. 58–61 (1993).
Wadhwa R. et al., "Protein Markers for Cellular Mortality and Immortality," *Mutat. Res.* 256:243–254 (1991).
Wadhwa, R. et al., "Differential Subcellular Distribution in mortal and Immortal Mouse and Human Fibroblasts," *Exper. Cell Res.* 207:442–448 (Aug. 1993).
Wadhwa, R. et al., "Induction of Cellular Senescence by Transfection of Cytosolic Mortalin cDNA in NIH 3T3 Cells," *J. Biol. Chem.* 268:22239–22242 (Oct. 1993).
Wadhwa, R. et al., "Spontaneous Immortalization of Mouse Fibroblasts Involves Structural Changes in Senescence Inducing Protein, Mortalin," *Biochem. Biophys. Res. Commun.* 197:202–206 (Dec. 1993).
Wadhwa, R. et al., "Identification of a Novel Member of Mouse hsp70 Family," *J. Biol. Chem.* 268:6615–6621 (Mar. 1993).

*Primary Examiner*—Toni R. Scheiner
*Attorney, Agent, or Firm*—Fulbright & Jaworski L.L.P.

[57] ABSTRACT

The intracellular distribution of mortalin is used to determine the complementation group of tumor cells. Also disclosed are the gene sequences that encode mortalin and the amino acid sequence of the mortalin proteins.

6 Claims, 4 Drawing Sheets

Figure 1

Figure 3 A, B, & C

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2155 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Murine ( v i i ) IMMEDIATE SOURCE:
        ( B ) CLONE: mortalin ( x i ) SEQUENCE DESCRIPTION: SEQ ID NO:1:

```
CGTTTCCAGA  AGCGTAGCAC  CACCGTGCAC  GCAGCTCCGG  GCCCGTGGGT  GTTGGTTCTT      60

GCCCTCGTAA  CCCCCTCTGT  CCAGCCACCA  TGATAAGCGC  CAGCAGAGCC  GCGGCCGCGC     120
```

-continued

| | | | | | |
|---|---|---|---|---|---|
|GTCTCGTGGG|CACCGCTGCG|TCCCGGAGCC|CCGCAGCCGC|CCGTCCCCAG|GATGGCTGGA 180|
|ATGGCCTTAG|CCATGAGGCT|TTTAGATTTG|TTTCAAGAAG|AGATTATGCA|TCAGAAGCAA 240|
|TCAAGGGTGC|AGTGGTTGGT|ATTGATTTGG|GTACTACTAA|CTCCTGTGTG|GCTGTTATGG 300|
|AGGGCAAACA|AGCAAAGGTC|CTGGAGAATG|CTGAAGGTGC|CAGAACTACC|CCTTCTGTGG 360|
|TTGCCTTTAC|AGCAGATGGA|GAACGACTTG|TTGGTATGCC|AGCAAACGG|CAAGCTGTCA 420|
|CCAATCCAAA|CAATACCTTC|TATGCTACTA|AGCGTATTAT|TGGACGACGA|TATGATGACC 480|
|CTGAAGTACA|GAAAGACACT|AAGAATGTTC|CTTTTAAAAT|TGTCCGTGCC|TCCAATGGTG 540|
|ATGCTTGGGT|TGAGGCTCAT|GGAAAACTCT|ATTCTCCAAG|TCAGATTGGA|GCATTTGTGT 600|
|TGATGAAGAT|GAAAGAGACT|GCAGAAAATT|ACTTGGGCCA|CACAGCAAAA|AATGCTGTGA 660|
|TCACAGTCCC|TGCTTATTTC|AATGATTCAC|AGCGACAGGC|CACTAAGGAT|GCTGGCCAGA 720|
|TATCTGGGCT|AAATGTGCTT|CGAGTGATCA|ATGAGCCTAC|AGCTGCTGCT|CTAGCTTACG 780|
|GTCTGGACAA|ATCTGAAGAT|AAAGTCATTG|CTGTGTATGA|TTTAGGTGGT|GGAACCTTTG 840|
|ACATTTCTAT|CCTGGAAATT|CAGAAAGGAG|TGTTTGAGGT|GAAATCTACC|AATGGGGACA 900|
|CTTTCTTAGG|AGGGGAAGAC|TTTGACCAAG|CTTTGTTGCG|GCACATTGTC|AAGGAGTTCA 960|
|AGAGAGAGAC|AGGGGTTGAT|TTGACCAAAG|ACAACATGGC|GCTTCAGAGG|GTTCGGGAAG 1020|
|CTGCTGAGAA|GGCTAAATGT|GAACTTTCCT|CATCTGTGCA|GACTGACATC|AACTTGCCAT 1080|
|ACCTTACCAT|GGATGCTTCT|GGACCAAAGC|ATTGAATAT|GAAGCTGACT|CGAGCTCAGT 1140|
|TTGAAGGCAT|TGTCACAGAT|CTAATCAAGA|GAACTATTGC|TCCGTGTCAG|AAAGCTATGC 1200|
|AGGATGCAGA|AGTCAGCAAG|AGTGACATAG|GAGAAGTGAT|TCTGGTTGGT|GGCATGACAA 1260|
|GGATGCCCAA|GGTTCAGCAG|ACTGTACAAG|ATCTTTTTGG|CAGAGCCCCG|AGTAAAGCTG 1320|
|TTAATCCTGA|TGAGGCTGTA|GCCATCGGAG|CTGCCATCCA|GGGAGGTGTG|TTGGCTGGTG 1380|
|ACGTTACAGA|CGTGCTGCTC|CTGGATGTCA|CTCCCCTCTC|TCTGGGTATT|GAGACTCTGG 1440|
|GAGGCGTCTT|TACCAAACTT|ATTAATAGGA|ACACCACTAT|TCCAACCAAA|AAGAGCCAGG 1500|
|TGTTTTCTAC|TGCTGCTGAT|GGACAAACTC|AAGTAGAGAT|TAAAGTGTGT|CAGGGGGAAC 1560|
|GAGAGATGGC|TGGAGACAAC|AAACTTCTAG|GACAGTTCAC|TTTGATTGGA|ATTCCCCCAG 1620|
|CCCCTCGTGG|AGTGCCCCAG|ATTGAAGTTA|CATTTGACAT|TGATGCCAAT|GGGATTGTGC 1680|
|ACGTTTCTGC|CAAAGATAAA|GGCACTGGTC|GTGAGCAACÀ|GATTGTAATC|CAGTCTTCTG 1740|
|GTGGATTAAG|CAAAGATGAT|ATTGAAAATA|TGGTTAAAAA|TGCAGAGAAG|TACGCTGAGG 1800|
|AAGACCGCAG|GAAGAAGGAA|CGTGTTGAAG|CAGTTAATAT|GGCTGAAGGA|ATTATTCATG 1860|
|ACACAGAAAC|CAAGATGGAA|GAATTTAAGG|ACCAGTTGCC|TGCTGATGAG|TGCAACAAGC 1920|
|TAAAGGAAGA|GATTTCCAAA|GTGAGAGCGC|TCCTTGCTCG|AAAGGACAGT|GAGACAGGAG 1980|
|AGAACATCAG|GCAGGCAGCA|TCTTCCCTAC|AGCAGGCGTC|ATTGAAACTC|TTCGAAATGG 2040|
|CGTACAAAAA|GATGGCATCT|GAACGGGAAG|GTTCTGGAAG|TTCTGGCACT|GGGGAACAGA 2100|
|AGGAAGATCA|GAAGGAAGAG|AAACAGTAAT|CGTGGCAGTG|CATTGTGGAG|CCAGA 2155|

( 2 ) INFORMATION FOR SEQ ID NO:2:

( i ) SEQUENCE CHARACTERISTICS:
        ( A ) LENGTH: 679 amino acids
        ( B ) TYPE: amino acid
        ( C ) STRANDEDNESS: single
        ( D ) TOPOLOGY: linear ( i i ) MOLECULE TYPE: protein (iii) HYPOTHETICAL: NO (vi) ORIGINAL SOURCE:
    (A) ORGANISM: Murine (vii) IMMEDIATE SOURCE:
    (B) CLONE: mortalin (xi) SEQUENCE DESCRIPTION: SEQ ID NO:2:

| Met | Ile | Ser | Ala | Ser | Arg | Ala | Ala | Ala | Arg | Leu | Val | Gly | Thr | Ala |
|---|---|---|---|---|---|---|---|---|---|---|---|---|---|---|
| 1 | | | | 5 | | | | | 10 | | | | | 15 |
| Ala | Ser | Arg | Ser | Pro | Ala | Ala | Ala | Arg | Pro | Gln | Asp | Gly | Trp | Asn | Gly |
| | | | 20 | | | | | 25 | | | | | 30 | | |
| Leu | Ser | His | Glu | Ala | Phe | Arg | Phe | Val | Ser | Arg | Arg | Asp | Tyr | Ala | Ser |
| | | 35 | | | | 40 | | | | | | 45 | | | |
| Glu | Ala | Ile | Lys | Gly | Ala | Val | Val | Gly | Ile | Asp | Leu | Gly | Thr | Thr | Asn |
| | 50 | | | | | 55 | | | | | 60 | | | | |
| Ser | Cys | Val | Ala | Val | Met | Glu | Gly | Lys | Gln | Ala | Lys | Val | Leu | Glu | Asn |
| 65 | | | | | 70 | | | | | 75 | | | | | 80 |
| Ala | Glu | Gly | Ala | Arg | Thr | Thr | Pro | Ser | Val | Val | Ala | Phe | Thr | Ala | Asp |
| | | | | 85 | | | | | 90 | | | | | 95 | |
| Gly | Glu | Arg | Leu | Val | Gly | Met | Pro | Ala | Lys | Arg | Gln | Ala | Val | Thr | Asn |
| | | | 100 | | | | | 105 | | | | | 110 | | |
| Pro | Asn | Asn | Thr | Phe | Tyr | Ala | Thr | Lys | Arg | Ile | Ile | Gly | Arg | Arg | Tyr |
| | | 115 | | | | 120 | | | | | | 125 | | | |
| Asp | Asp | Pro | Glu | Val | Gln | Lys | Asp | Thr | Lys | Asn | Val | Pro | Phe | Lys | Ile |
| | 130 | | | | | 135 | | | | | 140 | | | | |
| Val | Arg | Ala | Ser | Asn | Gly | Asp | Ala | Trp | Val | Glu | Ala | His | Gly | Lys | Leu |
| 145 | | | | | 150 | | | | | 155 | | | | | 160 |
| Tyr | Ser | Pro | Ser | Gln | Ile | Gly | Ala | Phe | Val | Leu | Met | Lys | Met | Lys | Glu |
| | | | | 165 | | | | | 170 | | | | | 175 | |
| Thr | Ala | Glu | Asn | Tyr | Leu | Gly | His | Thr | Ala | Lys | Asn | Ala | Val | Ile | Thr |
| | | | 180 | | | | | 185 | | | | | 190 | | |
| Val | Pro | Ala | Tyr | Phe | Asn | Asp | Ser | Gln | Arg | Gln | Ala | Thr | Lys | Asp | Ala |
| | | 195 | | | | 200 | | | | | 205 | | | | |
| Gly | Gln | Ile | Ser | Gly | Leu | Asn | Val | Leu | Arg | Val | Ile | Asn | Glu | Pro | Thr |
| | 210 | | | | | 215 | | | | | 220 | | | | |
| Ala | Ala | Ala | Leu | Ala | Tyr | Gly | Leu | Asp | Lys | Ser | Glu | Asp | Lys | Val | Ile |
| 225 | | | | | 230 | | | | | 235 | | | | | 240 |
| Ala | Val | Tyr | Asp | Leu | Gly | Gly | Gly | Thr | Phe | Asp | Ile | Ser | Ile | Leu | Glu |
| | | | | 245 | | | | | 250 | | | | | 255 | |
| Ile | Gln | Lys | Gly | Val | Phe | Glu | Val | Lys | Ser | Thr | Asn | Gly | Asp | Thr | Phe |
| | | | 260 | | | | | 265 | | | | | 270 | | |
| Leu | Gly | Gly | Glu | Asp | Phe | Asp | Gln | Ala | Leu | Leu | Arg | His | Ile | Val | Lys |
| | | 275 | | | | 280 | | | | | 285 | | | | |
| Glu | Phe | Lys | Arg | Glu | Thr | Gly | Val | Asp | Leu | Thr | Lys | Asp | Asn | Met | Ala |
| | 290 | | | | | 295 | | | | | 300 | | | | |
| Leu | Gln | Arg | Val | Arg | Glu | Ala | Ala | Glu | Lys | Ala | Lys | Cys | Glu | Leu | Ser |
| 305 | | | | | 310 | | | | | 315 | | | | | 320 |
| Ser | Ser | Val | Gln | Thr | Asp | Ile | Asn | Leu | Pro | Tyr | Leu | Thr | Met | Asp | Ala |
| | | | | 325 | | | | | 330 | | | | | 335 | |
| Ser | Gly | Pro | Lys | His | Leu | Asn | Met | Lys | Leu | Thr | Arg | Ala | Gln | Phe | Glu |
| | | | 340 | | | | | 345 | | | | | 350 | | |
| Gly | Ile | Val | Thr | Asp | Leu | Ile | Lys | Arg | Thr | Ile | Ala | Pro | Cys | Gln | Lys |
| | | 355 | | | | 360 | | | | | 365 | | | | |
| Ala | Met | Gln | Asp | Ala | Glu | Val | Ser | Lys | Ser | Asp | Ile | Gly | Glu | Val | Ile |

-continued

|   |   |   |   |   | 370 |   |   |   |   | 375 |   |   |   |   | 380 |   |   |
|---|---|---|---|---|---|---|---|---|---|---|---|---|---|---|---|---|---|
| Leu 385 | Val | Gly | Gly | Met | Thr 390 | Arg | Met | Pro | Lys | Val 395 | Gln | Gln | Thr | Val | Gln 400 |
| Asp | Leu | Phe | Gly | Arg 405 | Ala | Pro | Ser | Lys | Ala 410 | Val | Asn | Pro | Asp | Glu 415 | Ala |
| Val | Ala | Ile | Gly 420 | Ala | Ala | Ile | Gln | Gly 425 | Gly | Val | Leu | Ala | Gly 430 | Asp | Val |
| Thr | Asp | Val 435 | Leu | Leu | Leu | Asp | Val 440 | Thr | Pro | Leu | Ser | Leu 445 | Gly | Ile | Glu |
| Thr | Leu 450 | Gly | Gly | Val | Phe | Thr 455 | Lys | Leu | Ile | Asn | Arg 460 | Asn | Thr | Thr | Ile |
| Pro 465 | Thr | Lys | Lys | Ser | Gln 470 | Val | Phe | Ser | Thr | Ala 475 | Ala | Asp | Gly | Gln | Thr 480 |
| Gln | Val | Glu | Ile | Lys 485 | Val | Cys | Gln | Gly | Glu 490 | Arg | Glu | Met | Ala | Gly 495 | Asp |
| Asn | Lys | Leu | Leu 500 | Gly | Gln | Phe | Thr | Leu 505 | Ile | Gly | Ile | Pro | Pro 510 | Ala | Pro |
| Arg | Gly | Val 515 | Pro | Gln | Ile | Glu | Val 520 | Thr | Phe | Asp | Ile | Asp 525 | Ala | Asn | Gly |
| Ile | Val 530 | His | Val | Ser | Ala | Lys 535 | Asp | Lys | Gly | Thr | Gly 540 | Arg | Glu | Gln | Gln |
| Ile 545 | Val | Ile | Gln | Ser | Ser 550 | Gly | Gly | Leu | Ser | Lys 555 | Asp | Asp | Ile | Glu | Asn 560 |
| Met | Val | Lys | Asn | Ala 565 | Glu | Lys | Tyr | Ala | Glu 570 | Glu | Asp | Arg | Arg | Lys 575 | Lys |
| Glu | Arg | Val 580 | Glu | Ala | Val | Asn | Met | Ala 585 | Glu | Gly | Ile | Ile | His 590 | Asp | Thr |
| Glu | Thr | Lys 595 | Met | Glu | Glu | Phe | Lys 600 | Asp | Gln | Leu | Pro | Ala 605 | Asp | Glu | Cys |
| Asn | Lys 610 | Leu | Lys | Glu | Glu | Ile 615 | Ser | Lys | Val | Arg | Ala 620 | Leu | Leu | Ala | Arg |
| Lys 625 | Asp | Ser | Glu | Thr | Gly 630 | Glu | Asn | Ile | Arg | Gln 635 | Ala | Ala | Ser | Ser | Leu 640 |
| Gln | Gln | Ala | Ser | Leu 645 | Lys | Leu | Phe | Glu | Met 650 | Ala | Tyr | Lys | Lys | Met 655 | Ala |
| Ser | Glu | Arg | Glu 660 | Gly | Ser | Gly | Ser | Ser 665 | Gly | Thr | Gly | Glu | Gln 670 | Lys | Glu |
| Asp | Gln | Lys 675 | Glu | Glu | Lys | Gln |   |   |   |   |   |   |   |   |   |

MORTALIN AND METHODS FOR DETERMINING COMPLEMENTATION GROUP ASSIGNMENT OF CANCER CELLS

This invention was supported with Government funds (NIH AG 05333). The Government has certain rights in this invention.

FIELD OF THE INVENTION

The present invention is in the field of recombinant DNA technology. This invention is directed to mortalin, to gene sequences that encode mortalin and anti-mortalin antibodies. The invention further concerns the use of such compounds to determine the complementation group of cancer cells.

BACKGROUND OF THE INVENTION

Normal human diploid cells have a finite potential for proliferative growth. Thus, as the aging process occurs, the capacity of cells to proliferate gradually diminishes. The loss of cellular proliferative capacity of cells in culture is termed "senescence," and is the in vitro analog of aging (Hayflick, L. et al., *Exper. Cell Res.* 25:585 (1961); Hayflick, L. et al., *Exper. Cell Res.* 37:614–636 (1965); Norwood, T. H. et al., In: *Handbook of the Biology of Aging* (2nd ed.), Finch, C. E. et al. (eds.) Van Nostrand, New York pp. 291–311 (1985); Goldstein, S., *Science* 249:1129–1133 (1990); Smith, J. R., *Monogr. Devel. Biol.* 17:193–208 (1984); Smith, J. R. et al. Exper. *Gerontol.* 24:377–381 (1989), all herein incorporated by reference). Experimental evidence suggests that the age-dependent loss of proliferative potential may be the function of a genetic program (Orgel, L. E., *Proc. Natl. Acad. Sci.* (U.S.A.) 49:517 (1963); De Mars, R. et al., *Human Genet.* 16:87 (1972); Buchwald, M., *Mutat. Res.* 44:401 (1977); Martin, G. M. et al., *Amer. J. Pathol.* 74:137 (1974); Smith, J. R. et al., *Mech. Age. Dev.* 13:387 (1980); Kirkwood, T. B. L. et al., *Theor. Biol.* 53:481 (1975).

Indeed, the onset of senescence and aging are accompanied by significant changes in the profile of genes that are expressed. Through an analysis of such changes, researchers have identified unique mRNAs that are amplified in senescent cells in vitro (West, M. D. et al., *Exper. Cell Res.* 184:138 (1989); Giordano, T. et al., *Exper. Cell Res.* 185:399–406 (1989); Lumpkin, C. K. et al., *Science* 232:393–395 (1986)), thus suggesting that cellular senescence is mediated by an inhibitor of DNA synthesis (Spiering, A. I. et al., *Exper. Cell Res.* 179:159–167 (1988); Pereira-Smith, O. M. et al., *Exper. Cell Res.* 160:297–306 (1985); Drescher-Lincoln, C. K. et al., *Exper. Cell Res.* 153:208–217 (1984); Drescher-Lincoln, C. K. et al., *Exper. Cell Res.* 144:455–462 (1983)). The recognition of such changes has prompted efforts to clone the genes that encode the factors that control cellular senescence and proliferative capacity (Kleinsek, D. A., *Age* 12:55–60 (1989); Sierra, F. et al., *Molec. Cell. Biol.* 9:5610–5616 (1989); Pereira-Smith, O. M. et al., J Cell. Biochem. (Suppl.0 (12 part A)) 193 (1988); Kleinsek, D. A., Smith, J. R., *Age* 10:125 (1987)). Smith, J. R. (PCT Patent Appln. Publication No. WO 93/12251) describes senescent cell derived inhibitors of DNA synthesis.

Although the proliferative capacity of a cell is believed to be carefully regulated, cells can, through mutation or viral infection, lose their ability to respond to such regulatory factors and thereby re-acquire a capacity to proliferate. For cells cultured in vitro, this process is referred to as immortalization. In vivo, such uncontrolled cellular proliferation is a defining characteristic of cancer.

I. The Complementation Groups of Tumor Cells

Insight into the control of cellular proliferation has been gained from studies in which normal and immortal cells have been fused to form heterokaryons. Such studies have demonstrated that the quiescent phenotype of a normal cell is dominant over the proliferative phenotype of an immortalized carcinoma cell of a immortalized transformed cell (Bunn, C. L. et al., *Exper. Cell Res.* 127:385–396 (1985); Pereira-Smith, O. M. et al., *Somat. Cell Genet.* 7:411–421 (1981); Pereira-Smith, O. M. et al., *Science* 221:964–966 (1983); Muggleton-Harris, A. et al., *Somat. Cell Genet.* 6:689–698 (1980)).

Normal diploid somatic cells undergo a limited number of population doublings in culture (Cristofalo, V. J. et al., *Exp. Cell Res.* 76:419–427 (1973); Goldstein, S., *Science* 249:1129–1133 (1990); Hayflick, L., *Mutat. Res.* 256:69–80 (1991)) in contrast to tumor derived cells which can proliferate unabated. The former are widely accepted as a model for aging at the cellular level (Hayflick, L., *Mutat. Res.* 256:69–80 (1991); Schneider, E. L. et al., *Proc. Natl. Acad. Sci. USA* 73:3584–3588 (1976)) and the latter of a system which accepted as a model for aging at the cellular level and the latter offer a system which can be exploited to investigate the mechanisms that limit cell division potential and those that permit unlimited cell division. There have been many studies documenting the cellular changes that accompany senescence (Harley, C. B., *Mutat Res.* 256:271–282 (1991); Holiday, R., *J. Gerontol Biol. Sci.* 45:B36–41 (1990); Macieira-Coelho, A., *Mutat. Res.* 256:81–104 (1991); Sherwood, S. W. et al., *Proc. Natl. Acad. Sci. USA* 85:9086–9090 (1989)).

Theories as to the molecular mechanisms underlying senescence fall into two broad categories depending on whether their authors consider that senescence is caused by (i) random accumulation of errors in macromolecules or (ii) genetically programmed processes. Much evidence has been accumulated in favor of a normal genetic program being responsible for expression of the senescent phenotype. Its converse, immortalization, is an essential step in the full transformation of cells to tumorigenicity (O'Brien, W. et al., *Proc. Natl. Acad. Sci. USA* 83:8659–8663 (1986)) and in fact it has been proposed that cellular senescence is a mechanism for tumor suppression in human cells (Sager, R., *Science* 246:1406–1412 (1989)). Hybrids obtained from the fusion of normal cells with immortal cells have limited division potential (Bunn, C. L., et al., *Exper. Cell Res.* 127:385–396 (1980); Pereira-Smith, O. M. et al., *Science* 221:964–966 (1983); Muggleton-Harris, A. et al., *Somat. Cell Genet.* 6:689–698 (1980)) indicating that the phenotype of cellular senescence is dominant and immortality results from recessive changes in normal regulatory genes. Further, fusion of different immortal human cells with each other yields in some case hybrids which exhibit limited division potential while the fusion of other pairs of immortal cells yields immortal hybrids (Pereira-Smith, O. M. et al., *Science* 221:964–966 (1983)). Such complementation assays have led to the assignment of 30 immortal human cell lines to four complementation groups (Ning, Y. et al., *Mutat Res.* 256:303–310 (1991); Pereira-Smith, O. M. et al., *Proc. Natl. Acad. Sci. USA* 85: 6042–6046 (1988)). Microcell mediated chromosome transfer studies have defined chromosomes 1 and 4 as carriers of senescence genes; the nature and the function of these genes remains to be defined (Ning, Y. et al., *Proc. Natl. Acad. Sci. USA* 88:5635–5639 (1991)).

Pereira-Smith, O. M. et al. demonstrated that pairwise fusions between different immortalized cells occasionally resulted in hybrids that had lost their capacity to proliferate (Pereira-Smith, O. M. et al., *Proc. Natl. Acad. Sci.* (*U.S.A.*) 85:6042–6046 (1988)). By systematically conducting a pairwise analysis, four complementation groups were identified (A, B, C, and D). The fusion of cells having the same complementation group created hybrids that maintained the immortalized character of the parental cells. In contrast, when immortalized cells of different complementation groups were fused, the normal genes of one parent "complemented" the deficient mutant genes of the other, and the resulting hybrids became senescent. This discovery suggested the possibility that a small number of undefined and unidentified genes or pathways might control the ability of a cell to proliferate (Pereira-Smith, O. M. et al., *Proc. Natl. Acad. Sci.* (*U.S.A.*) 85:6042–6046 (1988)).

A capacity to readily determine the complementation group of a tumor cell would provide a valuable means for assessing the severity of the disease, and thus aid in determining the aggressiveness that must be used to treat the cancer. Moreover, a sensitive means for discerning tumor cells in micro-tumors, or for determining whether a tumor contains different classes of tumor cells would greatly be of great assistance in the diagnosis and treatment of cancer. The present invention provides such methods.

SUMMARY OF THE INVENTION

The present invention concerns, in part, the recognition of a gene sequence that encodes a protein ("mortalin") and that is expressed differentially in tumor and normal cells. The cellular expression of mortalin differs in complementation group A, B, C and D cells. Thus, mortalin, mortalin-encoding gene sequences, probes of such gene sequences and anti-mortalin antibody can be used to determine the complementation group of cancerous cells.

In detail, the invention provides a method for determining the complementation group of an immortalized cell (especially a tumor cell), which comprises:

(A) determining the intracellular distribution of a mortalin in the cell; and (B) correlating the determined distribution with the distribution of mortalin exhibited by cells of complementation group A, B, C or D.

The invention is particularly concerned with the embodiments wherein in step (A), the cell is incubated with an anti-mortalin antibody, the antibody being detectably labeled, and wherein the distribution of the intracellular mortalin is determined by detecting the labeled antibody.

The invention also provides the embodiments wherein the antibody is a polyclonal antibody or a monoclonal antibody.

The invention is also directed to a nucleic acid molecule, substantially free of its natural contaminants, and comprising a sequence encoding a mortalin, especially wherein the molecule has a sequence present in SEQ ID NO:1. The invention also includes a nucleic acid molecule capable of specifically hybridizing to the a mortalin-encoding nucleic acid molecule.

The invention also includes a mortalin protein, substantially free of its natural contaminants, and having the sequence of SEQ ID NO:2.

BRIEF DESCRIPTION OF THE FIGURES

FIG. 1 provides the cDNA sequence encoding the mortalin of MEC cells. The figure also presents the amino acid sequence of the mortalin protein.

FIG. 2A shows the distribution in normal human lung fibroblasts (MRC-5) and the cells, HT1080, HeLa, 143TK- and A549, representative of complementation groups A, B, C and D respectively, as observed under epifluorescence microscope. FIG. 2B provides a schematic presentation of mortalin localization in mortal and immortal cells of mouse and human origin. Four kinds of intracellular distribution found in the members of four complementation groups, A, B, C and D, of immortality is shown in addition to the uniformly distributed cytosolic mortalin in normal cells.

FIGS. 3A, 3B, and 3C provide a depiction of confocal laser micrographs showing the intracellular distribution of mortalin representative of complementation group A (FIG. 3A), group C (FIG. 3B) and group D (FIG. 3C).

DETAILED DESCRIPTION OF THE INVENTION

I. The Determinants of Cellular Proliferation

Figure 2A:
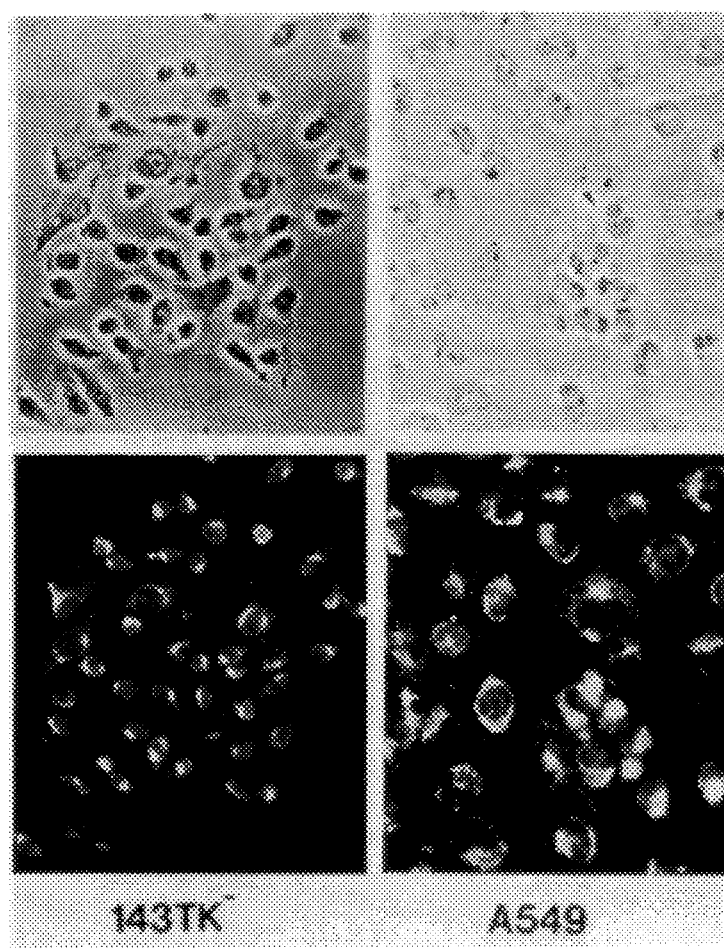
FIGS. 2A and 2B show the intracellular distribution of mortalin in various cell types.

The present invention derives, in part, from the recognition that tumor cells fall into one of four complementation groups (Pereira-Smith, O. M. et al., *Proc. Natl. Acad. Sci.* (*U.S.A.*)85:6042–6046 (1988); Pereira-Smith, O. M. et al., *J. Cell. Physiol.* 144:546–549 (1990); Ning, Y. et al., *Proc. Natl. Acad. Sci.* (*U.S.A.*)88:5635–5639 (1991); Pereira-Smith, O. M. et al., *J. Cell. Physiol.* 143:222–225 (1990)). This recognition suggests that, like many genetic diseases (e.g. cystic fibrosis, hemophilia, Tay-Sachs, etc.), cancer originates from a mutation in one of a small set of genetic loci. The identification of the complementation group that has been mutated in a particular tumor is of substantial medical importance. The neoplastic phenotype is recessive to the normal phenotype Pereira-Smith, O. M. et al., *Science* 221:964–966 (1983). Thus, once a tumor has been determined to belong to a particular complementation group, the genetic elements responsible for that complementation group may be administered to the tumor cells in treatment of the cancer. Similarly, an awareness of the complementation group of a tumor cell can be used to correlate the invasiveness of the tumor, or its sensitivity to conventional antineoplastic regimens.

II. Mortalin

A search for genes involved in senescence and immortalization using mouse embryonic fibroblast (MEF) system has led to the identification of a novel protein, mortalin (Wadhwa, R. et al., *Biochem. Biophys. Res. Commun.* 178:269–275 (1991); Wadhwa, R. et al., *Mutat. Res.* 256:243–254 (1991); Wadhwa, R. et al., *J. Biol. Chem.* 268:6615–6621 (1993)). Differences in the intracellular distribution rather than the presence or absence of this protein clearly distinguishes normal and immortal phenotypes (Wadhwa, R. et al., *Exp. Cell Res.* 207:442–448 (1993)). The differential cellular distribution in normal MEF versus immortal NIH 3T3 cells does not involve any detectable biochemical modifications of the protein (Kaul, S. C. et al., *Biochem. Biophys. Res. Commun.* 193:348–355 (1993)), but rather is the outcome of minor changes in the primary structure of the molecule (Wadhwa, R., et al., *J. Biol. Chem.* 268:22239–22242 (1993)). Mortalin is conserved as a 66-kDa protein in human cells and consistent with observations in mouse cells exhibits the differential distribution associated with the normal and immortal phenotype in studies of MRC-5 and HT1080 cells, respectively (Wadhwa, R., et al., *J. Biol. Chem.* 268:22239–22242 (1993)). The characteristics of mortalin and its genetic locus are discussed in detail below.

The invention includes polynucleotides that encode mortalin, as well as oligonucleotide fragments that are specifically complimentary to mortalin mRNA. A molecule is said to be specifically complementary to a mortalin mRNA or DNA molecule if it is capable of hybridizing to such molecule but is substantially incapable of hybridizing to other mRNA or DNA molecules that may be present in a reaction vessel. Molecules that encode mortalin may be used to express abundant quantities of the molecule, and hence can facilitate the production of antibodies used in the diagnosis of cancer cells.

The invention also includes the use of antisense molecules to the entire, or a portion of, mortalin mRNA. Such molecules can be used as probes of mortalin expression, and thus can be used to distinguish between normal and neoplastic cells.

III. The Use of Mortalin in the Determination of Complementation Group Assignment The present invention exploits the cellular distribution characteristics of mortalin by recognizing that such distribution characteristics can be correlated with the complementation group of tumor cells, and hence can be used to define the complementation group of any immortalized cell. As used herein, the term immortalized cell refers to any cell that has escaped normal proliferative control. Examples of such cells include tumor cells, transformed cells in culture, virally infected cells, cells of individuals suffering from progeria or other diseases of accelerated aging, etc.

In particular, an analysis of the mortalin distribution in immortal human cell lines that have been assigned to one of the four different complementation groups has revealed the existence of four distinct patterns of mortalin distribution. These patterns differed from the distribution seen in normal cells and permitted an absolute correlation to the four complementation groups. Cell lines assigned to the same group exhibit similar intracellular distribution of mortalin. Abnormal mortalin distribution was found to occur in all immortal cells studied and thus appeared to be a common end-point of each of the putative genetic pathways leading to immortalization. The observations also support the genetic evidence from cell fusion experiments that indicate that members of the same complementation group have been immortalized by similar mechanisms which differ from those involving members of other groups. The present invention thus emphasizes the role of mortalin in cellular senescence and immortalization and offers substantial supporting proof of the importance of the four complementation groups of indefinite division.

The molecules of the present invention may thus be used to diagnose the predisposition of an individual to cancer, and to determine which of the four complementation group pathways has been altered. Such information can be correlated against the accumulated data of amenability of such tumors, or their refractiveness, with respect to a particular chemotherapeutic agent or regime.

Moreover, the identification of the gene sequences of the determinants of cellular proliferation permits the development of determinant-specific probes that can be used (in conjunction with an amplification procedure, such as PCR) to assess whether an individual carries a mutation in one of the determinants. The capacity to evaluate the presence of such mutations provides an extremely sensitive method for diagnosing cancer. As such, the method can be employed at an extremely early stage, and thereby provide the physician with greater flexibility in treating the cancer.

Most preferably, such diagnosis will exploit antibodies reactive against mortalin. In one embodiment, such antibodies will be polyclonal and derived from an animal such as a mouse, rat, rabbit, monkey, etc. In an alternate embodiment, monoclonal antibodies will be employed.

The present invention thus provides a highly sensitive immunoassay suitable for detecting and/or quantitating the presence of mortalin in a sample. As used herein, the term "sample" is intended to encompass biological specimens derived from a human or other animal source (such as, for example, blood, stool, sputum, mucus, serum, urine, saliva, teardrop, a biopsy sample, an histology tissue sample, a PAP smear, etc.) including samples derived a cellular preparation (such as a cellular extract, lysate, cytosol, etc.). The most preferred samples are cellular samples or fractions of cellular extracts. As will be understood, the sample may need to be diluted with buffer, or concentrated (as with an evaporator or lyophilizer) in order to ensure that the amount of mortalin contained in the sample is within the detection limits of the assay.

Suitable polyclonal antibodies can be obtained by immunizing an animal with mortalin, and then isolating the immunoglobulin (e.g., IgG) fraction from the animal's serum. Suitable monoclonal antibodies are preferably produced by immunizing mice with the purified mortalin, either produced recombinantly, or via the purification of mortalin from natural sources. BALB/c mice are preferred for this purpose, however, equivalent strains may also be used. The animals are preferably immunized with approximately 25 μg of purified mortalin that has been emulsified 1:1 in a suitable adjuvant (such as TiterMax adjuvant; Vaxcel, Norcross, Ga.). Immunization is preferably conducted at two intramuscular sites, one intraperitoneal site, and one subcutaneous site at the base of the tail. An additional i.v. injection of approximately 25 μg mortalin is preferably given in normal saline three weeks later. After approximately 11 days following the second injection, the mice may be bled and the blood screened for the presence of anti-mortalin antibodies. Preferably, a direct binding ELISA is employed for this purpose.

Most preferably, the mouse having the highest anti-mortalin titer is given a third i.v. injection of approximately 25 μg mortalin. The splenic leukocytes from this animal may be recovered 3 days later, and are then permitted to fuse, most preferably, using polyethylene glycol, with cells of a suitable myeloma cell line. A preferred myeloma cell line is the P3X63Ag8.653 myeloma cell line. Hybridoma cells are selected by culturing the cells under "HAT" (hypoxanthine-aminopterin-Thymine) selection for about one week. The resulting clones may then be screened for their capacity to produce monoclonal antibodies ("mAbs") to mortalin ("anti-mortalin"), again preferably by direct ELISA.

High level production of the anti-mortalin mAbs may be obtained using nude mice. Nude mice are preferably primed with 0.5 ml of 2,6,10,14-tetramethypentadecane (Aldrich, Milwaukee, Wis.). After approximately 5 days, each clone is harvested, pelleted, and resuspended in sterile PBS to a final density of approximately $2.5 \times 10^6$ cell/ml. A pair of nude mice were injected for each monoclonal antibody. Antibody may be recovered from the ascites fluid of the animals, and is preferably lipocleaned with Seroclear (Calbiochem, San Diego, Calif.) following vendor specifications. The mAbs may then be further purified, preferably using a GammaBind Plus Sepharose column (Pharmacia, Uppsala, Sweden). Eluted MAb is preferably concentrated and dialyzed against saline. The concentration of the antibody may be determined using absorbance of light at 280 nm. Monoclonal antibodies can be isotyped using the Mouse MonoAB ID KIT (HRP) (Zymed, San Francisco, Calif.). Biotinylated MAB (b-mAb) were generated for each clone as described by (Harriman, G. R., In: *Current Protocols in Immunology*, vol. 1., Coligan, J. E. et al., eds., Greene Publishing Associates and Wiley-Interscience, New York, N.Y., p. 6.5.1 (1991)) for use in ELISA.

Most preferably, the immunoassay will be conducted in situ, on cell preparations or biopsied tissue. The assay of mortalin distribution may, however, be performed by separating a cell into substituent fractions (such as a cytosolic fraction, a membrane fraction, a perinuclear fraction, a nuclear fraction, etc.).

Most preferably, the antibody will be detectably labeled so as to facilitate the analysis. Suitable labels include a radioisotope, a paramagnetic atom, a fluorescent moiety, an enzyme, etc. In an alternative embodiment, the molecules can be labeled with reagents such as biotin, in order to, for example, facilitate their recovery, and/or detection.

In lieu of employing antibodies, fragments of antibodies that retain binding specificity may be employed. Examples of such alternatives include (F(ab'), F(ab')$_2$ fragments. The fragments can be directly used to assay mortalin expression, or they can be combined with fragments of other antibodies in order to form non-naturally occurring "divalent" or "multivalent" antibodies. Such antibodies could, for example, therefore possess the capacity to bind to multiple epitopes of mortalin, or to an epitope of mortalin and an epitope of another molecule.

Quite apart from their use in diagnosing the complementation state of immortalized cells, the antibodies of the present invention can be employed to enable a rapid recovery of substantially pure mortalin from either recombinant or natural sources. (e.g. cell extracts). Thus, such molecules can be used in large scale affinity chromatography to effect the removal of mortalin from a supernatant. For such purpose, the antibodies of the present invention can be bound to a resin, such as sepharose. The treated resin can be incubated, either in batch, as a slurry, or, more preferably, as a continuous throughput column in order to effect such recovery.

Having now generally described the invention, the same will be more readily understood through reference to the following examples which are provided by way of illustration, and are not intended to be limiting of the present invention, unless specified.

EXAMPLE 1

Purification of Mortalin

Microcell fusion studies of normal human cells and a variety of transformed cells have shown that the immortal phenotype is infrequently inherited by hybrids even if they inherit many transformed phenotypes, indicating that the expression of the genes responsible for transformation is not directly involved in immortalization (Matsumura, T., et al., *Exper. Cell Res.* 125:453–457 (1980); Pereira-Smith, O. M. et al., *Somat. Cell Genet.* 7:411–421 (1981)). Such studies have also indicated that cellular senescence is dominant over cellular immortality, and that immortality arises as the result of recessive dysfunctions or alterations in the genetic program that controls cellular proliferation (Pereira-Smith, O. M. et al., *Science* 221:964–966 (1983)).

Hybrids of mouse embryonic fibroblasts ("MEF") and the immortal cell line, MN48-1 (a oubain-resistant and 6-thioguanine resistant clonal derivative of NIH 3T3 cells) exhibited a senescent phenotype. By having such a system of natural and conditional ageing in mouse fibroblasts, wherein, unlike the human systems, secondary influences of chemical and viral agents could be eliminated, it was possible to screen for proteins whose expression was tightly linked to the mortal (i.e., parent MEF as well as heterogeneous hybrid cell populations) or immortal (MN48-1) phenotypes. The methods used to identify such proteins are described by Wadhwa, R. et al., *J. Biol. Chem.* 268(9):6615–6621 (1993), which reference is herein incorporated by reference in its entirety).

To identify such differentially expressed proteins, embryonic fibroblasts were isolated and cultured (Wadwha, R. et al., *Biochem. Biophs Res. Commun.* 178:269–275 (1991)). Cell hybrids were generated by 50% polyethylene glycol 6000-aided fusion of MEF cells and the MN48-1 cell line. Fibroblasts, grown to about 90% confluency in 10-cm culture dishes, were fractionated into nuclear, cytosolic and membrane fractions as described by Resh, M. D. et al. (*J. Cell. Biol.* 100:409–417 (1985)), except that protease inhibitors such as leupeptin (1 µg/ml), pepstatin (10 µg/ml), and phenylmethylsulfonyl fluoride (1 µg/ml) were added to the fractionation buffers.

Figure 1:
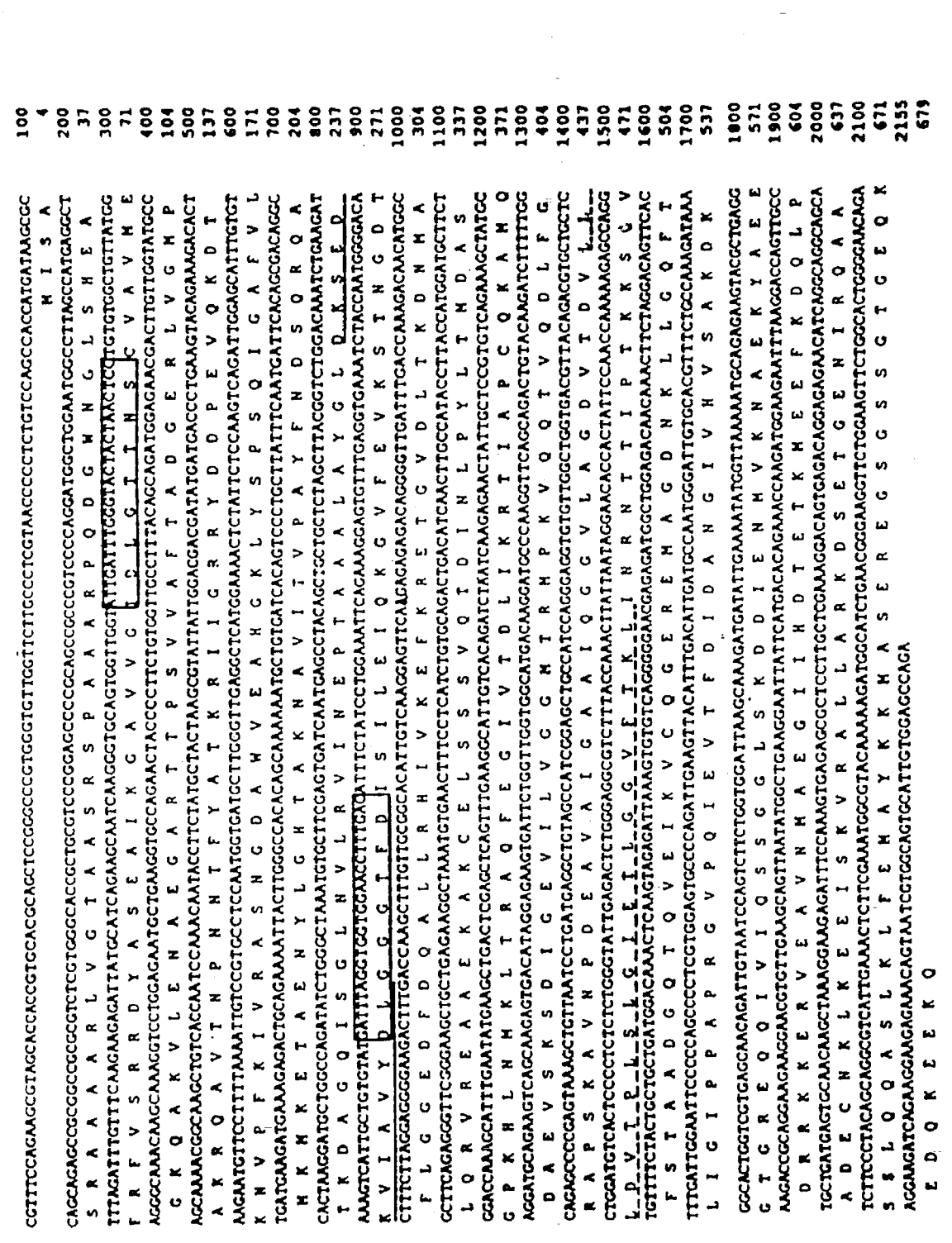

A protein of 66 kD (termed "p66") was identified in the cytostolic fractions of MEP and in the cytosolic fractions of the mortal hybrids of MEF and MN48-1. This protein was not detected in immortal cells such as MN48-1, NIH3T3 or RS-4 (a spontaneous, immortalized clone of MEF). The identified p66 protein was subsequently termed "mortalin." The amino acid sequence of mortalin is disclosed in FIG. 1 (SEQ ID NO:2), and in Wadhwa, R. et al., (*J. Biol. Chem.* 268(9):6615–6621 (1993), which sequence is herein incorporated by reference).

The mortalin protein was eluted from SDS-polyacrylamide gels and purified by passage through a Mono Q column. 50 µof purified protein in Freund's complete adjuvant was injected into a female New Zealand White Rabbit at multiple subcutaneous sites on the animal's back. A second injection was given two weeks later with 50 µg of mortalin emulsified with incomplete Freund's adjuvant. The rabbit was subsequently boosted at 2-week intervals with 100 µg of mortalin and bled on the tenth day after boosting.

A western blot analysis was conducted using the polyclonal antisera. Thirty micrograms of protein, separated by SDS-polyacrylamide gel electrophoresis, was electroblotted onto BA85 (Schleicher & Schüll) nitrocellulose membranes and visualized with the anti-mortalin antisera. Immunocomplexes were visualized with alkaline phosphatase-conjugated anti-rabbit immunoglobulin G. The polyclonal antisera identified a single protein band in the cytosolic fractions of mortal cells; the band could not be detected in immortalized cells.

Mortalin has significant homology to heat shock proteins, and in particular to the hsp70 family of heat shock proteins (Wadhwa, R. et al., *J. Biol. Chem.* 268(9):6615–6621 (1993)). Despite such homology, mortalin was not heat shock inducible. The amino and carboxy domains of mortalin differ significantly from the sequences of other heat shock family members. These regions are believed to be important to the biological activity of the protein.

EXAMPLE 2

Cloning of Mortalin cDNA cDNA encoding the mortalin protein was isolated by immunoscreening an MEF cDNA library. Approximately $5 \times 10^6$ plaques from an MEF cDNA library that had been prepared in λZAPII were screened with anti-mortalin antibody. Three clones were identified (10-1, 4-2, and 7-2) that contained overlapping fragments of the mortalin cDNA. The MEF cDNA library was rescreened with a 600 base pair PstI fragment of clone 4-2, and an extended clone (4-2-1) was obtained having additional 5' sequence. The cDNA defined by these clones was designated mot-1.

The isolation of these clones permitted the determination of the complete cDNA sequence of the mortalin gene. The cDNA sequence of the mortalin gene is shown in FIG. 1 (SEQ ID NO:1) and in Wadhwa, R. et al., (*J. Biol. Chem.* 268(9):6615–6621 (1993), which sequence is herein incorporated by reference).

The cDNAs encoding the mortalin gene fragments were transcribed and translated in vitro, and found to produce protein products that could be immunoprecipitated by the anti-mortalin antisera. The estimated size of the complete mortalin molecule was 75 kD, indicating the presence of peptide(s) to be cleaved during maturation of the protein.

EXAMPLE 3

Biological Activity of Mortalin

To assess the biological activity of mortalin, anti-mortalin antibodies were microinjected into MEF cells. The IgG fraction (1.5 mg/ml) of anti-mortalin antiserum (or serum obtained from the animals prior to the induction of anti-mortalin antibodies) was microinjected into MEF cells. Microinjection was performed directly on cells growing on four-chambered glass slides, 2 mm grid dishes, or coverslips using an Olympus IMT2 microscope with the SYF2 Inject Scope attachment. Control injections were performed with IgG fraction prepared from preimmune sera. Injected cells were distinguished from non-injected cells by adding 1 µg/ml FITC-dextran (Sigma Chemical Corp.) to the IgG fraction, and recorded with an RFC attachment (Olympus Corp.). The cells were fixed and stained with fluoroscein isothiocyanate (FITC)-labeled anti-rabbit IgG (1:1000 in phosphate buffered saline with 2% bovine serum albumin) after 9 hours of injection.

Microinjection was performed on sensescent MEF cell. grown on a 35 mm culture dish at about 40–50% confluency. Injection of FITC-dextran was found to affect cell viability by 20–30%, however microinjection of anti-mortalin stimulated cell division at about 48–72 hours post injection. The effect continued for 6–7 days after which the cells regained their senescent phenotype and did not further proliferate. The effect was observed in several independent experiments.

The mortalin protein does not appear to undergo phosphorylation, and does not act as a kinase in the absense of ATP and Mg; the protein does not appear to have an ATP binding activity.

EXAMPLE 4

Differential Distribution of Mortalin

As indicated above, mortalin was identified in the cytosolic fraction of senescent cells, but was not detected in the cytosolic fraction of immortal cells. In order to determine whether the protein is expressed in immortal cells, such cells were examined by indirect immunostaining (Wadwha, R. et al., *Exper. Cell. Res.* 207:442–448 (1993), herein incorporated by reference in its entirety). For such studies, cells were plated on poly-D-lysine-coated four chamber glass slides at densities ranging from $10^3$ to $10^4$ cells per well. After 24 hours, when cells had attached to the surface and spread well, they were washed three times with cold phosphate buffered saline (PBS) and fixed with a prechilled methanol/acetone/(1/1, v/v) mixture for 5 minutes on ice. Fixed cells were washed with PBS, permeabilized with 0.1% Triton-X in PBS for 10 minutes, and blocked with 2% bovine serum albumin (BSA) in PBS for 20 minutes. They were incubated with anti-mortalin antibody (1:600 in PBS with 2% BSA) or anti-tubulin antibody (Chemicon, U.S.A.) for 2–3 hours at room temperature, washed with PBS with 0.1% Triton-X and then incubated with FITC-conjugated anti-rabbit IgG for 30 minutes. After 6–8 washings in PBS with 0.1% Triton-X, cells were overlaid with a coverslip, with Fluoromount (Difco) and examined using an Olympus BH-2 microscope with epifluorescence optics on a Carl Zeiss confocal laser scanning microscope.

Visualization of protein revealed that the mortalin fluorescence was of a granular nature, scattered throughout the cytoplasm of senescent MEF and hybrid cells. All of ten hybrid cell lines tested invariably exhibited uniform granular scattering of mortalin-dependent fluorescence in cytoplasm. In contrast, however, immortalized cells such as MN48-1, NIH 3T3 cells or the RS4 MEF immortalized derivative, exhibited a mortalin fluorescence in the perinuclear region, with some cells showing juxtanuclear concentration. The anti-tubulin antibody control showed no difference in protein locations, thus indicating that the difference in mortalin fluorescence was not an artifact of the different cell morphology of mortal and immortal cells.

Fractionation of the extracts revealed that although the mortalin was not present in the cyosolic fractions of immortalized cells, it could be detected in the membrane and nuclear fractions, albeit at much lower concentrations. An immunoprecipitation assay with L-[$^{35}$S]methionine-labeled whole cell lysates showed the presence ofin NIH 3T3 cells and MN48-1 cells. The protein was present at approximately one half the level at which it was found in the mortal cells. These observations suggested that the mortalin was located within the cytoskeleton component actin of the cells. Indeed, immunoprecipitation of actin with anti-actin antibody resulted in the co-precipitation of an anti-mortalin antibody reactive protein. This co-precipitant was found to have a molecular weight of 66 kD, confirming that in immortalized MN48-1 and 3T3 cells the mortalin was localized to the cytoskeleton.

To extend the above observations to human cells, mortalin distribution was determined in normal human lung (MRC-5) and skin (TIG) fibroblasts, and in the human fibrosarcoma line HT1080 (N-ras$^+$), and in SV40-transformed human lung fibroblasts (GM639) and GM 847). Upon Western analysis, a 66 kD protein was immunoprecipitated by the anti-mortalin antibody.

As in the case of the murine cells, the normal cells exhibited a granular staining of mortalin throughout their cytoplasm. The immortalized human cells showed juxtanuclear staining; mortalin was not seen in the cytoplasm of any of the immortal human cells.

Thus, in summary, immortalized cells are not devoid of mortalin, but rather possess protein similar enough in structure to be recognized by anti-mortalin antibody. However, in contrast to normal cells the protein was localized to the perinuclear region.

EXAMPLE 5

Variations in Mortalin Structure

The recognition that both immortal and normal cells contained a mortalin protein suggested that minor differences in protein structure might be responsible for the divergent properties exhibited by such cells and that the perinuclear and cytosolic mortalins might have slightly different protein structures. Thus, a cDNA library was prepared from NIH 3T3 cell cDNA using the λZAPII vector (Stratagene) and used to obtain the mortalin-encoding cDNA of NIH 3T3 cells. The cloning method, and the sequences of the mortalin protein and cDNA of 3T3 cells is described by Wadhwa, R. et al., (*J. Biol. Chem.* 268(30):22239–22242 (1993), which reference is herein incorporated by reference in its entirety). The library was screened using a 1.6 kb EcoRI fragment of the mot-1 cDNA of the MEF cells as a hybridization probe.

Four overlapping clones were obtained, which were sequenced from both directions. The gene defined by these clones was designated mot-2. The proteins encoded by these cDNAs are designated mortalin (or mortalin-1or p66$^{mot-1}$) and mortalin-2 (or p66$^{mot-2}$). The full sequence of the mot-2 cDNA clones was derived by ligating sequences of deletion mutants into pBluescript SK+ (Stratagene) and was confirmed by reverse direction cloning and by dideoxy DNA sequencing.

Sequence comparisons of mot-1 cDNA (isolated from the MEF cDNA library) and the mot-2 cDNA (isolated from the NIH 3T3 cell cDNA library) exhibited differences at only two positions, i.e. at position 1941, the guanine of mot-1 was replaced with an adenine in mot-2 (G1941A); at position 1959, the cytosine of mot-1 was replaced with a guanine in mot-2 (C1959G). These changes in sequence cause the encoded mortalin to differ in two amino acids, i.e. at position 618, the valine of MEF mortalin is replaced by a methionine in 3T3 mortalin (V618M); at position 624, the arginine of MEF mortalin is replaced by a glycine in 3T3 mortalin (V618M). Secondary structure of the respective protein forms, p66$^{mot-1}$ and p66$^{mot-2}$, revealed that the change from arginine to glycine can introduce an additional turn in a helix.

Complete open reading frames (2.1 kilobase pairs) of mot-1 and mot-2 cDNA were cloned into pSRα, a eukaryotic expression vector and were transfected into NIH 3T3 cells. The transfected cells were selected by virtue of the resistance to G418 (1 mg/ml) conferred by the coexpression of a neomycin resistance determinant of the vector. The selected clones were studied for their morphology, division potential, and subcellular distribution of mortalin.

Transfection of mot-1 cDNA was found to have induced morphological alteration in the 3T3 cells. Cells showed senescent morphology as early as the first or second "splitting" (a "splitting" is a 1:5 dilution of cells into fresh medium ) in 60-mm culture dishes after the initial isolation of the clones. The transfected clones transfected with the mot-1 cDNA (positive transfectants) senesced in culture as they stopped dividing and could not be established like untransfected cells, vector-transfected cells, or cells transfected with a mot-1-containing vector in which the mot-1 cDNA was introduced in an antisense orientation. The positively transfected clones could not be passaged for more than three splittings in 60-mm culture dishes, which roughly corresponded to the maximum of 25 population doublings.

The expression of transfected cDNA was analyzed by immunoprecipitation from L-[$^{35}$S]methionine-labeled cell lysates by anti-mortalin antibody, which as indicated above recognizes both the cytosolic and perinuclear mortalin forms. The transfected clones showed about 2–3-fold increased expression of mortalin (as quantified from the radioactivity of immunoprecipitated protein by image analyzer) when compared to that of untransfected, vector-transfected, or antisense-transfected clones. By immunostaining observations under light and confocal laser microscopy, the transfected 3T3 clones were observed to exhibit the cytosolic spreading of mortalin-related immunofluorescence (indicating the induced expression of mot-1) in addition to the perinuclear localization (indicative of the endogenous expression of mot-2).

Northern analysis with 27-mer oligonucleotide probes specific to mot-1 and mot-2 (corresponding to bases 1938–1964, in the antisense direction of SEQ ID NO:1), including two alternative bases at 1941 and 1959 positions, could identify mot-1 and mot-2 transcripts in mot-1 transfectants, whereas only mot-2 is seen in NIH 3T3 and mot-1 in MEF cells. Such identification of only mot-1 and mot-2 transcripts in MEF and NIH 3T3 cells, respectively, supports the above mentioned cloning and immunostaining results. The set of experiments is dually informative in that:

(1) differences of two base pairs in cDNA with two corresponding changes in amino acids are sufficient for inducing the differential subcellular localization of protein. Product of mot- 1 expression (p66$^{mot-1}$) has potential to be distributed in cytosol even in immortal cells, which normally harbor mot-2 product (p66$^{mot-2}$) in the perinuclear region.

(2) Differentially distributed forms have different biological activities. The observations represent the mean of at least four independent experiments, wherein 81% of the isolated mot-1 transfectant clones senesced in contrast to 5% of controls (vector transfectants and antisense transfectants), which were lost in culture (probably due to the loss of G418 resistance). All the positive transfectants showed increased mortalin expression (in three independent sets of immunoprecipitation assays, sense transfectants showed 2.1 -, 2.4-, and 2.7-fold increased expression as compared to the untransfected, vector-transfected, and antisense-transfected controls) and cytosolic distribution.

Northern analysis though could not be extended to more than 20% of the cloned transfectants due to the limits imposed by acquired cellular mortality and thus the lack of enough amount of cellular RNA, more than 80% of the analyzed mot-1 transfectants could be detected for mot-1 transcript. The finding that the immortal cells acquired mortal phenotype by the induction of cytosolic protein is suggestive of its mortality inducing function and supports the above observations on transient stimulation of DNA synthesis by the microinjection of anti-mortalin antibody in senescent MEF. The mechanism of such acquisition of limited proliferation potential or the uplift of unabated proliferation of immortal cells by mot-1 transfection remains to be known.

The question of whether mot-2 cDNA has a defined biological activity such as immortalization or whether the latter is the consequence of loss of mortality was resolved by transfecting mot-2 cDNA into NIH 3T3 cells and early passage primary fibroblasts.

For such transfection experiments, mot-1 and mot-2 cDNA (complete open reading frame) were cloned into pSRα expression vector composed of human immunodeficiency virus promoter-enhancer and a neomycin resistance determinant in either a sense or an antisense orientations. The vectors were transfected into NIH 3T3 cells using a mammalian transfection kit (Stratagene). Transfectants were selected in 1 mg/ml in G418 supplemented growth medium (Dulbecco's modified Eagle's medium supplemented with 10% fetal calf serum). About 6–10 clones were isolated from each transfection by cloning rings, which were subsequently maintained in 500 μg/ml G418 supplemented medium. Daily observations on morphology and division rate were continued for about 4–6 weeks, during which some of the representative clones (in 35-mm culture dishes) were metabolically labeled with L-[$^{35}$S] methionine for immunoprecipitation ($10^6$ trichloroacetic acid-precipitable counts/minute used for each reaction). Immunoprecipitated protein was quantified using an image analyzer (BAS 2000, Fujix, Tokyo, Japan). All isolated clones were checked for cellular distribution of p66 protein by immunostaining as described by Wadwha, R. et al. (*Exper. Cell. Res.* 207:442–448 (1993)).

Transfection of mot-2 cDNA was found to mediate a 2–3 fold overexpression of mot-2 cDNA in primary and NIH 3T3 fibroblasts as seen by immunoprecipitation. Immunostaining revealed the overexpression of $p66^{mot-2}$ in NIH 3T3 cells to be concentrated, and perinuclearly distributed. It is significant to note that mot-2 transfectants did not show cytosolic distribution of mortalin, thus ruling out the apparent cytosolic distribution in mot-1 transfectants described above as the mere effect of overexpression. Furthermore, the transfection of mot-2 into primary fibroblasts induced the perinuclear form against their native cytosolic form. However, none of the MEF-mot-2 transfectants acquired an immortal phenotype, although 6% of the NIH 3T3/mot-2 transfectants were lost during culture. Apparently, the overexpression of mot-2 did not alter the cellular immortality phenotype; additionally, the induced mot-2 expression against the background of mot-1 did not induce immortality. In sum, the loss, rather the gain, of a biological function resulted in the spontaneous immortalization of the cells.

EXAMPLE 6

Isoelectric Focusing and Size Fractionation of Mortalin

As indicated above, the cytosolic form of mortalin ($p66^{mot-1}$) isolated from MEF cells differs from the perinuclear form ($p66^{mot-2}$) isolated from NIH 3T3 cells by only two amino acids. Whereas the former molecule induced cellular senescence in NIH 3T3 cells, the latter did not impart any effect on cellular phenotype.

To further analyze these related proteins, isoelectric focussing and subsequent size fractionation were conducted. Cells were thus grown in 60-mm dishes and harvested at 90% confluency. Cell pellets were washed in phosphate-buffered saline and then stored at −20° C. till further use. Alternatively, cells were metabolically labeled in the presence of L-[$^{35}$S]methionine (50 μCi/ml) for 6–8 h in methionine-free DMEM supplemented with 5% dialyzed fetal calf serum and harvested as above. The cell pellets were lysed in Nonidet P-40 lysis buffer (20 mM Tris (pH7.5), 1 mMEDTA, 1 mMEGTA, 0.1 mM phenylmethylsulfonyl fluoride, 150 mM NaCl, % Nonidet P-40) for 30 min on ice and the lysate obtained after centrifugation at 100, 000× g for 20 min at 4° C. were used for immunoprecipitation and two-dimensional analysis of mortalins with anti-mortalin antibody. Cell lysates containing 150 μg of total protein from primary fibroblasts (as estimated by the method of Bradford, M. M. (*Anal. Biochem.* 72:248–254 (1976)) using bovine serum albumin as a standard) and $5 \times 10^6$ cpm trichloroacetic acid-precipitable counts from indicated immortal cells were mixed and immunoprecipitated with anti-mortalin antibody (2 μl) on ice for 90 min. Immunocomplexes were absorbed onto protein A-Sepharose beads were solubilized in a urea lysis buffer (9.5M urea with 2% w/v Nonidet P-40, 1.6% ampholine (pH 5–8) (Pharmacia), 0.4% ampholine (pH 3–10) and 5% β-mercaptoethanol) and were separated on the pH gradient of 8 to 5 followed by size separation on a 7.5% SDS-polyacrylamide gel. The gel was stained with silver for visualization of cytosolically distributed mortalin from primary fibroblasts (cold lysate) and autoradiographed for visualization of perinuclearly distributed mortalin from immortal cell (metabolically labeled lysates). The gels were overlapped to see the separation of mortalins from indicated cells on single SDS-polyacrylamide gel.

Upon such isoelectric focusing and subsequent size separation of $p66^{mot-1}$ and $p66^{mot-2}$ on single SDS-polyacrylamide gel, $p66^{mot-1}$ was found to exhibit an additional slow migrating spot as compared to $p66^{mot-2}$. Perinuclear mortalin from immortal cell lines such as RS-4 (the spontaneous immortalized clone from MEF) and Balb/c 3T3, however, did not exhibit equivalent results though these cell lines harbor a mortalin having the same two amino acids as that of NIH 3T3 cells by reverse transcriptase polymerase chain reaction and sequence analysis. The data suggest that the mortalin-encoding locus undergoes specific and defined changes during cellular immortalization.

The synchronous two-dimensional analysis of the cytosolic and the perinuclear forms of mortalin suggested that the cytosolic mortalin ($p66^{mot-1}$) from C-MEF can be distinguished from the perinuclear mortalin ($p66^{mot-2}$) from NIH 3T3 cells, wherein the former separates as three very nearby spots aligning at the region of pI 5.9 and the latter lacks the slow migrating (more basic) spot. Since only one mot-1 transcript was detected in MEF cells by northern analysis, the two spots common to NIH 3T3 cells do not represent structurally very distinct form of protein. Rather, the absence of the slow migrating (more basic) spot in the NIH 3T3 sample may either reflect the change from arginine to glycine as described above or some undetectable minor modification of the protein. Furthermore, as indicated above, transfection of mot-1 cDNA induces cellular mortality in NIH 3T3 cells whereas the overexpression of mot-2 does not impart any detectable effect in these cells. Thus the two defined changes are associated with the biological function of the protein which seems to be mediated by differential cellular distributions.

Balb/c 3T3 and RS-4 cells are seen to harbor perinuclearly distributed mortalin. Both of these were found to exhibit mot-2-like structure, i.e., methionine at amino acid residue 618 and glycine at amino acid residue 624, as analyzed by localized reverse transcriptase polymerase chain reaction and sequencing. The data substantiated that the two reported changes are important and are sufficiently involved for the lack of cytosolically distributed mortalin and the escape from its senescence inducing function as described.

In view of the differential mobility of mortalins from C-MEF and NIH 3T3 cells, combinations such as MEF and Balb/c 3T3, and C-MEF & RS-4 cells, were evaluated. Surprisingly, the equivalent mobility shift was not observed under the similar experimental conditions when MEF and NIH 3T3 mortalins could reproducibly be differentiated. Thus the protein from RS-4 and Balb/c 3T3 cells though perinuclearly distributed may not be identical to that of NIH 3T3 cells. It is significant to note that i) if the above described differential separation of $p66^{mot-1}$ and $p66^{mot-2}$ is due to some minor chemical modification, such modification is not indispensable to escape from the senescence-inducing function of cytosolic mortalin, $p66^{mot-1}$ and ii) the heat shock induced translocation of mortalin from cytosolic to perinuclear localization was also not distinguished on two-dimensional gel which indicated that minor structural changes rather than the chemical modification are involved in the differential distribution of mortalin. Furthermore, the purified protein from MEF cells when mixed with L-[$^{35}$S] methionine labeled immunoprecipitated protein from NIH 3T3 cells and analyzed similarly, the differential separation of $p66^{mot-1}$ and $p66^{mot-2}$ was confirmed.

The data suggests the possibility that additional changes occur at the mortalin locus during immortalization of RS-4 and Balb/c 3T3 cells. The two above described changes are seen to be sufficient to escape from senescence inducing function of cytosolic mortalin (p66$^{mot-1}$), whereas the perinuclear mortalin (p66$^{mot-2}$) is seen to be biologically inactive. The biological significance of the additional implicated changes remains unknown.

EXAMPLE 7

Use of Cellular Mortalin Distribution in the Determination of Complementation Group Assignment The studies presented above suggested that mortalin played an important role in cell proliferation control, and that the minor changes in the gene which altered the intracellular localization of its product relate to the mortal and immortal phenotypes. The involvement of mortalin in the processes to cellular senescence were accordingly evaluated As indicated, immortal human fibroblasts-derived cell lines (such as HT1080 and GM847) were devoid of cytosolic spreading and exhibited a granular staining pattern, whereas normal fibroblasts (such as MRC-5 and TIG) showed cytosolic spreading of mortalin-related immunofluorescence (Wadwha, R. et al., *Exper. Cell. Res.* 207:442–448 (1993)). Normal human umbilical vein endothelial cells (HUVEC) also exhibited cytosolic immunofluorescence whereas its immortal clone (tHUE-2) showed perinuclear staining, texture of which was fibrous rather than the granular form observed in the case of HT 1080 and GM847. SUSM 1 cells were found to exhibit a fibrous perinuclear pattern like tHUE-cells and to present a pattern that was very distinct from that of HT 1080 cells. Realizing that SUSM I cells have been assigned to complementation group D whereas HT1080 and GM847 belong to group A (Pereira-Smith, O. M. et al., *Proc. Natl. Acad. Sci. USA* 85:6042–6046 (1988)) it was of interest to extend the observations to further cell lines in these and other complementation groups.

Cell lines representative of each of the four complementation groups for immortalization were used: GM847 (simian virus 40 SV40]-immortalized skin fibroblasts), VA13 (SV40-immortalized lung fibroblasts), EJ (bladder carcinoma with activated c-H-ras oncogene), HeLa (cervical carcinoma), GM2096SV9 (xeroderma pigmentosum skin fibroblasts immortalized with origin-defective SV40), T98G (glioblastoma), TE85 (osteogenic sarcoma), 143BTK-(TE85 secondarily transformed liver fibroblasts), A1698 (bladder carcinoma), wtB (SV40-immortalized Keratinocytes), J82 (bladder carcinoma), A549 (lung carcinoma), W138-ctl ($^{60}$Co-irradiated lung fibroblasts) CMV-Mj-HEL-1 (cytomeglaovirus-transformed lung fibroblasts), and HT1080 (fibrosarcoma with activated N-ras oncogene). Other cells studied were MeT-5A (pRSV-immortalized mesothelial cells) (Ke, Y., et al., *Am. J. Pathol.*, 134:979–991 (1989)), BEAS-2B/R1 (SV40-immortalized bronchial epithelial cells) (Ke, Y. et al., *Differentiation* 38:60–66 (1988); Reddell, R. R. et al., *Cancer Res.* 48:1904–1909 (1988)), HB56B/5T (pRSV-T immoralized bronchial epithelial cells) (Reddell, R. R. et al., *Int. J. Cancer* 48:764–773 (1991)), BET-1A (bronchial epithelial cells immortalized by transfection with an origin-defective SV40 early region expression plasmid, pRSV-T) (Reddell, R. R. et al., *Cancer Res.* 48:1904–1909 (1988)) and tHUE-2 (spontaneously immortalized clones from human umbilical vein endothelial cells, HUE) (Kobayashi, M. et al., *Human Cell.* 4:296–305 (1991)). MRC-5 (lung fibroblasts) and TIG-1 (skin fibroblasts) and HUE cells were used as normal controls.

The majority of the immortal and normal human cell cultures were maintained in Dulbecco's modified Eagle's minimal essential medium (DMEM) supplemented with 10% fetal calf serum (Biocell, U.S.A.). McT-5A, BEAS-2B/R1, HB56B5/T and BET-1A were cultured as described by Duncan, E. L. et al. (*Exp. Cell Res.* 205:337–344 (1993); Whitaker, N. J. et al., *J. Virol.* 66:1202–1206 (1992)). Endothelial cells were grown in MCDB151 medium (Sigma) supplemented with 15% fetal bovine serum, 5 ng/ml of heparin (Sigma) and 5 ng/ml of recombinant acidic fibroblast growth factor (FGF-1), tHUE-2 was maintained in AZF medium (Azinomoto, Japan) (Kobayashi, M. et al, *Human Cell.* 4:296–305 (1991)).

For indirect immunofluorescence studies, cells were plated on poly-D-lysine-coated four chambered glass slides at densities ranging from $10^3$ to $10^4$ cells per well. After 24 h when cells had attached to the surface and spread well they were washed 3 times with cold phosphate buffered saline (PBS) and fixed with a mixture of cold methanol/acetone (1:1, v/v) for 5 min on ice. Fixed cells were washed with PBS<permeabilized with 0.1% TritonX-100 in PBS for 10 min., and blocked with 2% bovine serum alburnin (BSA) in PBS for 20 min. They were incubated with anti-mortalin antibody (1:600 in PBS with 2% BSA) for 2–3 hours at room temperature, washed with PBS containing 0.1% TritonX-100 and then incubated with flourescein isothiocyanate (FITC)-conjugated anti-rabbit immunoglobulin G (IgG) for 30 min. After 6–8 washings in PBS with 0.1% Triton X-100, cells were overlaid with a coverslip using Fluoromount (Difco) mounting medium. The cells were examined on an Olympus BH-2 microscope with epifluorescence optics or on a Carl Zeiss confocal laser scanning microscope.

Figure 2B:
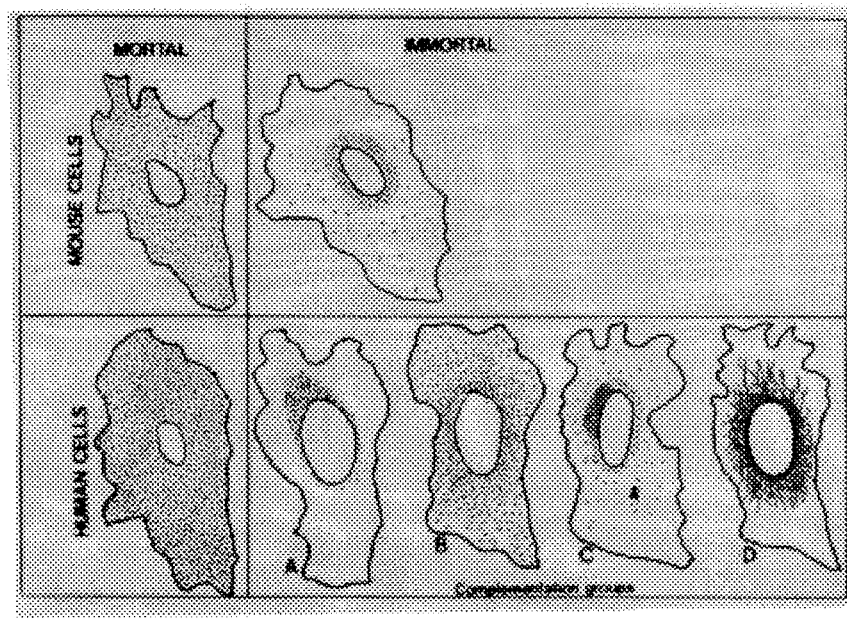

A 66-kDa protein was identified in all of the cell lines by western analysis with anti-mortalin antibody. The intracellular localization of mortalin, however, was distinct in members of the different complementation groups (FIG. 2A and 2B). EJ and VA13 which, like HT1080, and GM847 assign to complementation group A and are derived from different sources indicated in Table 1, displayed a granular juxtanuclear cap like staining (FIG. 3A). Group D members such as SUSM 1, A1698 and kmst-6 had perinuclear and fibrous staining (FIG. 3C). A549 lung carcinoma cell line which has not been firmly assigned to group D, but has been designated not A, not B and not C, also exhibited fibrous staining suggesting its assignment to group D. Group B members, HeLa, GM2096SV9, T98G and J82 were observed to have a gradient pattern of mortalin concentration decreasing from the nuclear membrane to the cell membrane. Cell lines assigned to group C, i.e., 143BTK, TE85 and CMV-Mj-HEL-1 showed a concentration of mortalin towards one side of the nucleus like an arch which is distinct from the pattern seen in the group A cell lines (FIG. 3B). Each cell line was submitted to at least three immunostainings and based upon the immunofluorescence patterns the sixteen cell lines could be assigned to the four previously defined complementation groups. One cell line, wtB, did not exhibit the immunostaining pattern which correlated with its complementation group assignment. wtB was observed to have perinuclear fibrous staining pattern like group D cell lines although it has been assigned to group A (Pereira-Smith, O. M. et al., *Proc. Natl. Acad. Sci. USA* 85:6042–6046 (1988)). It should be noted that characterization of assignment of wtB to complementation groups has not been extensive. It has been found to complement to yield the mortal phenotype with one member of group B and not with one member of group A (Pereira-Smith, O. M. et al., *Proc. Natl. Acad. Sci. USA* 85:6042–6046 (1988)). Information regarding its complementation with the members of groups C and D has not been obtained to date.

In support of the staining pattern of mortalin correlating with complementation group, it has been found that the immortal SV40-transformed cell line GM2096SV9, which was the exception assigned to group B, in fact has the intracellular distribution of mortalin similar to the other members of group B, HeLa, T98G and J82. Additionally, Whitaker et al. (Whitaker, N. J., et al., *J. Virol.* 66:1202–1206 (1992)) have categorized the immortal SV-40 transformed human bronchial epithelial cell line, BET-1A to group D which consistently exhibited fibruous and perinuclear staining similar to the other members of group D. It has also been determined by mortalin immunoflourescence pattern that the SV40 transformed cell line GM2096SV9 should be assigned to group B and that the BET-1A cell line should be assigned to group D rather than to group A (HT1080, VA13, GM847 and EJ). The intracellular distribution of mortalin in these SV-40 immortalized cells taken together with the results of Duncan et al. (Duncan, E. L., et al., *Exp. Cell Res.* 205:337–344 (1993)) substantiate the indication that SV-40-transformed cells can become immortalized via different genetic mechanisms, presumably involving loss of function of different genes required for the expression of senescent phenotype, and that a common outcome of different mechanisms may be the disruption of normal mortalin localization.

The three SV-40 transformed epithelial cell lines (MeT-5A, BEAS-2B/R1 and HB56B/5T) could not be assigned to a single complementation group by the hybrid complementation analysis (Duncan, E. L., et al., *Exp. Cell Res.* 205:337–344 (1993)). It is possible that these cell lines have lost the function of more than one of the putative senescence genes, in which case the pattern of mortalin distribution might not be easily predicted. However, MeT-5A cells have been found to exhibit the fibrous and perinuclear mortalin immunofluorescence similar to group D cells, with a small fraction of the cells having a juxtanuclear cap pattern similar to group A (15–20%); the gradient or the juxtanuclear arch patterns typical of groups B and C were not observed in this cell line. The mortalin pattern is therefore consistent with group D which is one of the groups (B, C, and D) to which MeT-5A cells were assigned (Duncan, E. L., et al., *Exp. Cell Res.* 205:337–344 (1993)).

The results indicate that the multiple group assignment could possibly be due to the presence of the small fraction of cells which have a group A like immunofluorescence. Similarly, the mortalin immunofluorescence pattern places HB56B/5T cells in group B, although the complementation analysis has assigned it to both groups B and D. The third cell line, BEAS-2B/R1, is placed in group B by mortalin distribution pattern in contrast to its complementation assignment to groups C and D (Duncan, E. L., et al., *Exp. Cell Res.* 205:337–344 (1993)) (Table 1).

Overall, of the cell lines assigned to a single complementation group, 17/18 had a corresponding mortalin distribution. Of the three cell lines that could not be assigned to a single complementation group, two had a mortalin distribution corresponding to one of the groups to which they were assigned. Further investigation will reveal the nature of the wtB and BEAS-2B/R1 cell lines. It is significant to note that none of the 21 immortal cell lines analyzed exhibited a pattern of uniform cytoplasmic mortalin distribution characteristic of normal cells, i.e., in all immortal cells studied, lack of a normal finite lifespan is associated with loss of cytosolic mortalin (and presumably loss of its normal function). Other evidence for the essential role of mortalin in cellular mortality include the following: (1) mortal hybrids obtained by the fusion of mortal and immortal mouse fibroblasts were found to have the uniform granular cytosolic mortalin distribution pattern characteristic of normal cells (Wadwha, R. et al., *Exper. Cell. Res.* 207:442–448 (1993)); (2) microinjection of an anti-mortalin antibody stimulated cell division in senescent mouse fibroblasts; and (3) transfection of a cDNA encoding cytosolic mortalin was able to induce senescence of immortal cells (Wadhwa, R., et al., *J. Biol. (Chem.* 268:22239–22242 (1993)). Independent recent studies by Bruschi et al. (Bruschi, S. A. et al., *J. Biol. Chem.* 268:23157–23161 (1993)) have identified mortalin as a major target for modification during S-(1, 1, 2, 2-Tetrafluoroethyl) L-cystein-induced in vivo nephrotoxicity.

The fact that the cytosolic distribution in mouse fibroblasts could transiently be changed to the perinuclear location by heat shock treatment (Kaul, S. C., et al., *Biochem. Biophys. Res. Commun.* 193:348–355 (1993)) and also that the cytosolic and perinuclear forms of mortalin from MEF and NIH3T2 cells exhibit minor structural differences indicate that the distinct secondary structure of the protein may represent the differentially distributed forms (Wadhwa, R. et al., *J. Biol. Chem.* 268:22239–22242 (1993)). It can be anticipated that the different complementation groups of immortality involve distinct changes in the secondary structure of protein. The possibility that these changes could be the result of secondary effects of some other primary genetic events cannot be overlooked. The induced expression of cytosolic mortalin in NIH 3T3 cells resulted in the cellular mortal phenotype, suggesting that the cytosolic mortalin has dominant mortality determining function. Studies of mortalin in complementing and non-complementing cell-cell hybrids may contribute significantly to an understanding of the mechanisms of cellular mortality and immortalization. The present data provide supporting evidence for the existence of distinct complementation groups for immortality and also proposes the central role of mortalin in the determination of cellular mortality and immortalization.

In sum, the dominance of cellular senescence over the immortal phenotype has been demonstrated by cell fusion experiments utilizing human and mouse cells. Mortalin, a novel 66-kDa member of the murine hsp 70 family of proteins, has recently been identified as a marker of the mortal phenotype by virtue of its characteristic cytosolic distribution in mortal cells. The present invention concerns, in part, the recognition that human cell lines can be assigned to one of the four complementation groups for immortality by determining the intracellular distribution of mortalin. In addition, various patters of mortalin immunostaining, i.e., granular-juxtanuclear cap, granular-gradient from nuclear to cell membrane, granular-juxtanuclear arch and fibrous-perinuclear, were found to characterize different cell lines. The data i) indicate that the intracellular distribution of mortalin can be used to distinguish mortal and immortal cells, confirming the association of mortalin with senescence; ii)provide confirmatory evidence for the existence of at least four different pathways of immortalization in human cells; and iii)indicate that mortalin is involved in processes that result in immortalization.

TABLE 1

| Cell line | Description | Group assigned | Mortalin Nature of immunostaining | Mortalin Localization |
|---|---|---|---|---|
| HT1080 | Fibrosarcoma (N-ras+) | A* | Granular | Juxtanuclear cap |
| VA13 | SV40-immortalized lung fibroblasts | A* | Granular | Juxtanuclear cap |
| EJ | Bladder carcinoma (H-ras+) | A* | Granular | Juxtanuclear cap |
| GM847 | SV40-immortalized skin fibroblasts (HPRT−, Lesch Nyhan) | A* | Granular | Juxtanuclear cap |
| wtB | SV40-immortalized keratinocytes | A* | Fibrous | Perinuclear |
| SUSM-1 | 4NQO-transformed liver fibroblasts | D* | Fibrous | Perinuclear |
| W138-ct1 | Coirradiated lung fibroblasts | D* | Fibrous | Perinuclear |
| A1698 | Bladder carcinoma (Ki-ras+) | D* | Fibrous | Perinuclear |
| HB56B/5T | pRSV-T immortalized bronchial epithelial cells | B, D** | Fibrous | perinuclear |
| MeT-5A | pRSV40 transformed mesothelial cells | B, C, D** | Fibrous | perinuclear |
| A549 | Lung carcinoma | Not A, not B, not C* | Fibrous | Perinuclear |
| BET1a | pRSV-T immortalized bronchial epithelial cells | D** | Fibrous | Perinuclear |
| tHUE-2 | Spontaneously immortalized human umbilical vein endothelial cells | — | Fibrous | Perinuclear |
| HeLa | Cervical carcinoma | B* | Granular | Gradient# |
| GM2096SV9 | Origin-defective SV40-immortalized XP skin fibroblasts | B* | Granular | Gradient# |
| BEAS-2B/R1 | SV40-immortalized bronchial epithelial cells | D, C** | Granular | Gradient# |
| T98G | Glioblastoma | B* | Granular | Gradient# |
| J82 | Bladder carcinoma | B* | Granular | Gradient# |
| TE85 | Osteogenic sarcoma | C* | Granular | Juxtanuclear arch |
| 143BTK− | TE85 secondarily transformed by Kirsten mouse sarcoma virus (Ki-ras+) | C* | Granular | Juxtanuclear arch |
| CMV-Mj-HEL-1 | Cytomegalovirus-transformed lung fibroblasts | C* | Granular | Juxtanuclear arch |

*Pereira-Smith, O. M. and Smith, J. R. (1988) Proc. Natl. Acad. Sci. USA 85, 6042–6046.
**Duncan et al. (1993) Expt. Cell Res. 205, 337–344.
Gradient from nuclear to cell membrane While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for determining the complementation group of an immortalized cell, which comprises:

(A) determining the intracellular distribution of a mortalin in said cell; and (B) correlating the determined distribution with the distribution of mortalin exhibited by cells of complementation group A, B, C or D.

2. The method of claim 1, wherein in step (A), said cell is incubated with an anti-mortalin antibody, said antibody being detectably labeled, and wherein the distribution of said intracellular mortalin is determined by detecting said labeled antibody.

3. The method of claim 1, wherein said immortalized cell is a tumor cell.

4. The method of claim 3, wherein said tumor cell is obtained from the biopsy of a tumor.

5. The method of claim 2, wherein said antibody is a polyclonal antibody.

6. The method of claim 2, wherein said antibody is a monoclonal antibody.

* * * * *